US006992073B2

(12) United States Patent
Xu et al.

(10) Patent No.: US 6,992,073 B2
(45) Date of Patent: Jan. 31, 2006

(54) USE OF N-ACETYL-D-GLUCOSAMINE IN THE MANUFACTURE OF A MEDICAMENT FOR TREATING CERVICAL EROSION

(75) Inventors: Qiwang Xu, Chongqing (CN); Junkang Liu, Chongqing (CN); Zetao Yuan, Chongqing (CN)

(73) Assignees: Third Military Medical University, Chinese People's Liberation Army, Chongging (CN); Bio-Wave Institute of Suzhou Hi-Tech New District Corporation, Ltd., Jiangsu (CN); Beijing Sino-HongKong Dafu Science & Technology of Biowave Co., Ltd., Beijing (CN)

( * ) Notice: Subject to any disclaimer, the term of this patent is extended or adjusted under 35 U.S.C. 154(b) by 0 days.

(21) Appl. No.: 10/469,268

(22) PCT Filed: Feb. 28, 2002

(86) PCT No.: PCT/CN02/00118

§ 371 (c)(1),
(2), (4) Date: Mar. 2, 2004

(87) PCT Pub. No.: WO02/067945

PCT Pub. Date: Sep. 6, 2002

(65) Prior Publication Data

US 2004/0138174 A1 Jul. 15, 2004

(51) Int. Cl.
*A01N 43/04* (2006.01)
*A61K 31/70* (2006.01)
(52) U.S. Cl. .................. 514/62; 514/967; 536/55.2
(58) Field of Classification Search .................. 514/62; 536/55.2
See application file for complete search history.

(56) References Cited

U.S. PATENT DOCUMENTS

| 5,116,615 A | 5/1992 | Gokcen et al. |
| 6,046,179 A * | 4/2000 | Murch et al. ................. 514/62 |
| 2002/0115115 A1 * | 8/2002 | Smith et al. ................. 435/7.8 |

FOREIGN PATENT DOCUMENTS

| CN | 1156026 A | 8/1997 |
| CN | 1156027 A | 8/1997 |
| CN | 1156028 A | 8/1997 |
| JP | 59013708 A2 | 1/1984 |
| JP | 63273493 | 11/1988 |
| JP | 2011505 A2 | 1/1990 |
| JP | 10-287570 | 10/1998 |
| WO | WO 87/02244 * | 4/1987 |
| WO | WO/A 8 702244 | 4/1987 |
| WO | WO 91/02530 | 3/1991 |
| WO | WO 93/14765 | 8/1993 |
| WO | WO 93/18775 | 9/1993 |
| WO | WO 97/18790 | 5/1997 |
| WO | WO 97/31121 | 8/1997 |
| WO | WO 99/53929 | 10/1999 |

OTHER PUBLICATIONS

International Search Report of PCT/CN02/00118, dated May 2, 2002.
U.S. Appl. No. 10/469,284, filed Aug. 28, 2003, Xu et al.

* cited by examiner

*Primary Examiner*—James O. Wilson
*Assistant Examiner*—Traviss C. McIntosh, III
(74) *Attorney, Agent, or Firm*—Christie, Parker and Hale, LLP

(57) ABSTRACT

The present invention has disclosed the use of N-acetyl-D-glucosamine in the manufacture of a medicament for treating cervical erosion. N-acetyl-D-glucosamine can resist the field planting of microorganism and control microorganism infection, and improve the symptoms of local exudation, tissue inflammatory oedema and pain and the like.

4 Claims, No Drawings

USE OF N-ACETYL-D-GLUCOSAMINE IN THE MANUFACTURE OF A MEDICAMENT FOR TREATING CERVICAL EROSION

CROSS-REFERENCE TO RELATED APPLICATION

This application is a National Phase Patent Application of International Application Number PCT/CN02/00118, filed on Feb. 28, 2002, which claims priority of Chinese Patent Application Number 01104884.0, filed on Feb. 28, 2001.

TECHNICAL FIELD

The present invention relates to the use of N-acetyl-D-glucosamine and pharmaceutical acceptable salts thereof in the manufacture of a medicament for treating cervical erosion.

BACKGROUND ART

Cervical erosion is a common disease in gynecology, it is caused by superficial defect formed by squamous epithelium necrosis and abscission at cervix and vagina, or eversion of the mucosa at cervical canal, it is expressed by the increase of exudation and secretion, congestion and oedema of cervix mucosa, microorganism infection and etc., and it is happened in the chronic cervix inflammation. This symptom is not only deferred and difficult to be cured and substantially influent the normal life, but it is also possible to be developed into cancer.

At present, in China and other countries, most of the treatment methods of the cervical erosion use physical therapy in clinic such as electric ironing, freezing, laser and other means to make erosive tissue to be necrotized and obscised, or use corrosive medicament such as potassium dichromate, silver nitrate etc. to destroy the erosive tissue; for serious patients, even use surgical operation to cut out the cervix or uterus. The therapies mentioned above would bring great pains to the patients; when removing erosive tissue, a lot of normal tissues will be involved. Other medicaments purchased from market generally use ethanol as solvent, so it has a strong stimulation, while the solute itself also has stimulation to cause pain and injure normal skin. Furthermore, most all of these products are functionally limited to sterilization, and have an effect to control infection, but destroy the equilibrium of microorganism state, and cannot cure the infection radically. Therefore, it is necessary all along to develop a medicament for treating cervix erosion in the field.

In the research of "bio-waves" theory, the present inventor has set up a bacterial wave growth model. Through researching, it is known that this wave is of its intrinsic regulation mechanism: some chemical substances are able to participate the regulation in the bio-wave process, so as to transform an abnormal periodic slow wave into a normal physiological chaotic quick wave, and this kind of substances are known as promoting wave factors. Through separating, purifying and identifying, it is determined that one of the factors is N-acetyl-D-glucosamine, the promoting wave function of which is shown in lubricating and protecting the cell. Many biochemical and physiological process of human body need the participation of the promoting wave factors, and it would lead to an abnormal state, if this kind of promoting wave factors is lacked in the living body.

N-acetyl-D-glucosamine is a chemical reagent. From the 1990's, it is continually used to treat pericementitis (WO9102530A1), microbiological infection (WO9718790-A3), intestinal inflammation (WO9953929A1), cornea disease (JP10287570A2), hypertrophy of the prostate (U.S. Pat. No. 5,116,615) and so on. It is also applied in cosmetology (JP59013708A2), shampoo preparation (JP2011505A2), tissue growth regulation agent (WO/A 8 702244), and etc., but it has not been used in the manufacture of a medicament for treating cervix erosion disease up to now.

The applicant of the present invention finds that N-acetyl-D-glucosamine is able to effectively treat cervix erosion, this discovery is extremely beyond people's expectation, because curing cervix erosion needs many assistant cooperation of controlling microorganism infection, resist local exudation, removing tissue inflammation oedema and pain, and improving tissue reparation and etc., so that doctors have to prescribe multiple medicaments combined with each other to cure the patients, but now it is found that a medicament with N-actyl-D-glucosamine as active component by itself is able to cure cervix erosion. Although the current techniques have disclosed the resistance for microorganism infection and tissue growth regulating functions of N-actyl-D-glucosamine, the discovery of the present application is quite a surprise to the people.

CONTENTS OF THE INVENTION

Therefore, the present invention is related to the use of N-acetyl-D-glucosamine and pharmaceutical acceptable salt thereof in the manufacture of a medicament for treating cervical erosion.

In addition, the present invention is related to a method for treating cervical erosion, including administrating to a patient who is in need thereof an effective amount of N-acetyl-D-glucosamine or pharmaceutical acceptable salts thereof.

The molecular formula of N-acetyl-D-glucosamine is $C_8H_{15}NO_6$, its structure is as follows:

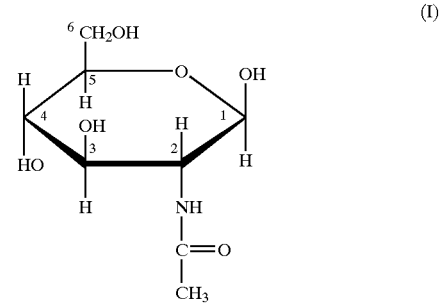

(I)

N-acetyl-D-glucosamine can be purchased in the market or prepared according to known methods. For instance, patent application WO97/31121 has disclosed a method for preparing N-acetyl-D-glucosamine from chitin by enzyme method, Japanese patent application JP63273493 has disclosed a method in which chitin is partially hydrolyzed into N-acetyl-chitose, and then it is treated with enzyme to obtain N-acetyl-D-glucosamine.

The pharmaceutical acceptable salts of N-acetyl-D-glucosamine that can be mentioned are the salts formed with pharmaceutical acceptable acids, for instance, the salts formed with inorganic acids, such as hydrochloride, hydrobromide, borate, phosphate, sulfate sulfite and hydrophosphate, and the salts formed with organic acids, such as citrate, benzoate, ascorbate, methyl sulfate, naphthalene-2-sulfonate, picrate, fumarate, maleate, malonate, oxalate, succinate, acetate, tartrate, mesylate, tosylate, isethionate, α-ketoglutarate, α-glyceryl phosphate and glucose-1-phosphate.

Generally, the compound of formula (I) of the present invention is formulated with one or more pharmaceutically acceptable excipients and/or carriers to prepare external-using preparations in the form of aqueous solution (lotion), emulsion, cream, ointment, suppository, and etc, for treating cervix erosion. The amount of the active substance is 0.26% of that of the whole preparation. The daily dosage of N-acetyl-D-glucosamine is 100~2000 mg for each person.

Though having no intention to be limited by any theories, the present inventor thinks that the effect of the compound of formula (I) for treating cervix erosion is affected by regulating the cellular redistribution of organism. The cellular redistribution refers to the continually replacement of the position of the organism cell or the position of the microorganism cell, and rhythmic replacement of gel-sol states of biological macromolecule in vivo. Through cellular redistribution in different level, N-acetyl-D-glucosamine is able to develop its special efficacy. The macroscopic replacements of cellular position have the wave growth characteristic. Through regulating the wave growth of the organism cell and microorganism cell to be normal, N-acetyl-D-glucosamine makes microorganism cannot be planted locally. In microorganism ecological efficacy, a method which mainly support normal bacterial colony to grow but not supplement ecological bacterial colony is able to avoid the problem of adaptability to field planting condition existed in the supplementing bacterial colony. In the aspect of repairing skin mucosa tissue, N-acetyl-D-glucosamine has a controlling effect for inflammation, injure, infection, exudation, and this is just the characteristic of the product of the invention which can be widely applied to control the symptom and carry out the treatment to solve the radical problem.

OPTIMAL MODE FOR CARRYING OUT THE INVENTION

The following experimental examples are used to illustrate the promoting wave function, low toxicity, effectiveness for resisting the field planting activity of microorganism, and clinic observation for treating cervix erosion of the compound of the present invention (the compound of formula (I)).

I. Promoting Wave Test of the Compound of Formula (I)
   1. Experimental Materials and Method:
   1.1 Samples: Pure Compound of Formula (I)
   1.2 Experimental Materials:
      Strain: Proteus Mirabilis, Lactobacilli.
      Culture medium: modified LB culture medium (the components of the composition are: trytones of 1%, yeast extract of 0.5%, sodium chloride 1%, glucose of 0.1%, TTC of 0.002% and pH=7.2~7.4).
   1.3 Experimental Method:
      The Proteus Mirabilis were inoculated at the center of LB plate, incubating at 37° C. for 9 hours, then there were concentric rings emerged, which were extended outward continually with an interval of 3 hours, and this was taken as a control; adding the compound of formula (I) with final concentration of 0.5% onto the LB plate, The Proteus Mirabilis were innoculated by the same method, cultured at 37° C., and the result showed that not only the concentric rings formed with an interval of 3 hours were emerged, comparing with the control, it can be seen that there were also many fine waves on each ring emerged.

Meanwhile, the result of liquid cultivation also shows that, the compound of formula (I) can improve the growth of Lactobacilli.

2. Experimental Results and Evaluation:
   The experiment adopts a bio-wave model which is used to research the promoting wave function of the compound of formula (I). It can be seen from the result that the compound of formula (I) was not only able to cause bacterial cell to reveal a normal bio-wave characteristic, but also cause the wave reveal finer wave mode, and these indicated that the compound of formula (I) have promoting function to bio-waves, and the promoting wave function is able to participate the reparation and re-distribution function of the cells of skin.

II. Toxicological Test of the Compound of Formula (I), including:
   1. acute toxicity test: including tests of administrating medicine by oral, Intravenous injection and maximum limit amount for administration;
   2. Ames test;
   3. micronucleus test of bone marrow cell of mouse;
   4. abnormal sexual test for the sperm of mouse;
   5. abnormal aberrance test for the chromosin of mouse's testis;
   6. chronic lethal test;
   7. subchronic toxicity ( feed for 90 days) test;
   8. traditional aberrance-inducing test;
      The results from these tests show that in the acute toxicity test of the compound of formula (I), the dosage more than 2 g/kg is taken, which is 300 times than the injection dosage for human being, but the acute toxicosis reaction had not appeared yet; in the long-period toxicity test, the maximum dosage has reached up to 1 g/kg, and after the treatment and observation for four weeks, there is no toxicosis reaction yet; and in the reproduction test, the mouse was fed with routine dosages from 7 mg/kg for 3 generations, it has been proved that the compound of formula (I) has no influence on the pregnancy, birth, nurse and the growth of baby mice, so it is proved that the compound of formula (I) is a substance without toxicity.

III. Test of Removing Pathogenic Microorganism by Resistance to Field Planting Action The results from in situ bacterial field planting, qualitative and quantitative determination tests show that the compound of formula (I) substantially has no sterilizing or bacteria-inhibiting effect, it is by the way of disabling pathogenic microorganism such as *Candida albicans,* vagina *Heamophilus* and etc. from field planting growth, so as to reach the aim of resisting infection.

IV. Clinic Test

A spray formulation of 2% N-acetyl-D-glucosamine was applied to human beings, up to the end of August 1999, there were 123 cases of patients to be observed in total. It can be seen from the result, compared with blank control group (without administrating medicament), and compared with positive medicament (AgNO$_3$) control group, the statistic analysis show that, the treatment group of the invention have obvious effect in view of positive medicament control group and blank control group in respect of the cure rate and effective rate, the spray formulation of N-acetyl-D-glucosamine has a remarkable curative effect to cervix erosion, the results of which is as follows:

|                              | Number of cases | cured | effective |
| ---------------------------- | --------------- | ----- | --------- |
| Treating group               | 83              | 48    | 15        |
| Positive medicament control group | 60         | 5     | 8         |
| Blank control group          | 40              | 2     | 6         |

What is claimed is:

1. A method of treating cervical erosion, comprising administrating to a subject in need of such treatment a therapeutically effective amount of a medicament including N-acetyl-D-glucosamine and/or a pharmaceutically acceptable salt thereof.

2. The method according to claim 1, wherein the medicament is externally administrated to the subject in the form of an aqueous solution, an emulsion, a cream, an ointment or a suppository.

3. The method according to claim 2, wherein the medicament is administered with a daily dosage of N-acetyl-D-glucosamine and/or pharmaceutically acceptable salt thereof ranging from about 100 to about 2000 mg.

4. A method of treating cervical erosion, comprising administering to a subject in need of such treatment, via the subjects vagina, a therapeutically effective amount of a medicament including N-acetyl-D-glucosamine and/or a pharmaceutically acceptable salt thereof.

* * * * *

UNITED STATES PATENT AND TRADEMARK OFFICE
CERTIFICATE OF CORRECTION

PATENT NO. : 6,992,073 B2
APPLICATION NO. : 10/469268
DATED : January 31, 2006
INVENTOR(S) : Xu et al.

It is certified that error appears in the above-identified patent and that said Letters Patent is hereby corrected as shown below:

On the Title Page

(73) Assignees: Delete "Third Military Medical University, Chinese People's Liberation Army, Chongging",
Insert -- Third Military Medical University, Chinese People's Liberation Army, P.R. of China, Chongqing --

(30) Foreign Patent Application Priority Data   Insert --(30) Foreign Patent Application Priority Data   Feb. 28, 2001 (CN) 01104884.0--

In the Claims

Column 6, line 11, Claim 4   Delete "subjects",
insert --subject's--

Signed and Sealed this

Sixth Day of March, 2007

JON W. DUDAS
*Director of the United States Patent and Trademark Office*